United States Patent [19]

Hogg

[11] 4,009,435
[45] Feb. 22, 1977

[54] APPARATUS FOR PRESERVATION AND IDENTIFICATION OF PARTICLES ANALYZED BY FLOW-THROUGH APPARATUS

[75] Inventor: Walter R. Hogg, Miami Lakes, Fla.

[73] Assignee: Coulter Electronics, Inc., Hialeah, Fla.

[22] Filed: Oct. 8, 1975

[21] Appl. No.: 620,658

Related U.S. Application Data

[63] Continuation-in-part of Ser. No. 496,178, Aug. 9, 1974, Pat. No. 3,924,947, which is a continuation-in-part of Ser. No. 407,811, Oct. 19, 1973, abandoned.

[52] U.S. Cl. .............................. 324/71 CP; 356/39; 356/36; 356/38; 356/71; 356/72; 356/73
[51] Int. Cl.² ................. G01N 33/16; G01N 27/00; G01N 51/00
[58] Field of Search ........... 324/71 CP; 356/36, 38, 356/39, 71, 72, 73

[56] References Cited
UNITED STATES PATENTS

| | | |
|---|---|---|
| 3,710,933 | 1/1973 | Fulwyler et al. .................. 209/3 |
| 3,910,702 | 10/1975 | Coril .............................. 356/72 |
| 3,924,947 | 12/1975 | Hogg .............................. 356/39 |

Primary Examiner—R. V. Rolinec
Assistant Examiner—Vincent J. Sunderdick
Attorney, Agent, or Firm—Silverman & Cass, Ltd.

[57] ABSTRACT

An apparatus for identifying particles such as cells in a liquid suspension includes a particle scanning device containing a suspension of the particles. The suspension moves in a stream through a sensing zone in the device, which, for example, may be a Coulter type particle detector, and out of the sensing device to a waste receptacle. As each particle in the suspension passes through the sensing zone, it will produce a particle pulse whose measurements represent at least one physical characteristic of the particle. A particle collecting substrate is positioned adjacent the stream departing the scanning device. A counting device, coupled to the scanning device and the substrate, operates only in response to the particle pulse for each sensed particle selected to develop a particular count signal and to direct the stream and the selected particle therein to a particular location on the substrate corresponding to the particular counting signal. A memory operates in response to the particle pulse to store the particle pulse measurements and count signal therein so that the particle locations on the substrate and measurements representing particle characteristics are correlated. The entire sequence of operation is inhibited during start up and stabilization of the apparatus operation, and during and after each particle selection. This ensures that the particle sensed and no other particle is deflected to the location and that the measurements of the particle characteristics at a substrate location and the counting signal for that substrate location are properly correlated and stored.

30 Claims, 2 Drawing Figures

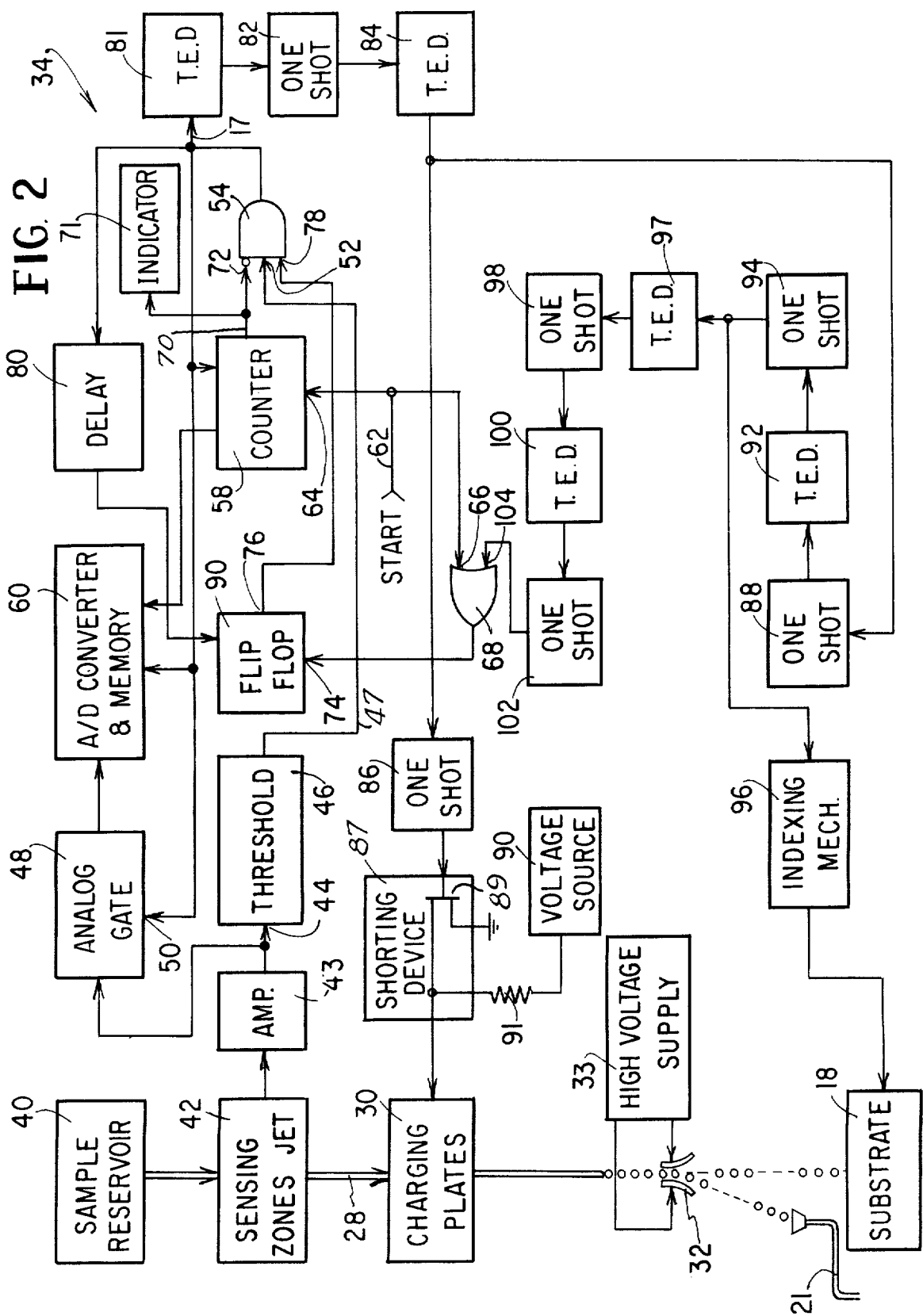

APPARATUS FOR PRESERVATION AND IDENTIFICATION OF PARTICLES ANALYZED BY FLOW-THROUGH APPARATUS

CROSS-REFERENCE TO RELATED APPLICATIONS

This application is a Continuation-in-Part of Application Ser. No. 496,178, filed Aug. 9, 1974, now Pat. No. 3,924,947, which is a Continuation-in-Part of Patent Application Ser. No. 407,811, filed Oct. 19, 1973 and now abandoned. All patent applications are owned by the same assignee.

BACKGROUND OF THE INVENTION

This invention relates to an apparatus for identifying and preserving particles and correlating them with their measured characteristics.

Many people have concerned themselves with the study of particle characteristics and especially the study of physiological cells. There are two schools of thought as to how best to study these cells.

Probably the earliest school taught flowing the cells one at a time through some type of sensing zone where a characteristic such as for example size or color is measured. This measurement may be counted and hence the cells themselves are counted. This technique is referred to as a "flow through" technique.

One of the most basic flow through type tools for measuring characteristics of particles at the present time is an electronic particle sensing device whose structure and operation are generally disclosed in U.S. Pat. No. 2,656,508. Structures incorporating the teachings of the aforementioned patent are often described as Coulter type particle detectors. The characteristics which can be measured electronically with instruments of this nature are particle size and parameters related to size along with the count of particles. Valuable information which can be gleaned no other way may be obtained through the techniques taught in U.S. Pat. Nos. 3,502,973 and 3,502,974. Many other characteristics of particles can be measured optically as well as electronically, and in recent times such measurements are done at relatively high speeds and in flow systems.

In all of these known apparatuses, the particles have their characteristics measured in gross, albeit individually, and as soon as the particles have passed the sensing zone where the measurements are actually made, the particles are discarded or comingled with others thereby losing their individual identities. In effect, the characteristics are measured and correlated statistically to a given sample, then the particles are discarded, thus precluding individual identification of the particles by trained observers. For the most part, both for industrial and medical applications, the data thus obtained can be somewhat satisfactory even though only gross sample can be preserved and further tested, and even though any particular date cannot be related to any single particle.

The second school taught the mechanical duplication of the function performed by a human observer such as a trained cytologist, and is referred to as "Pattern Recognition". In this procedure a sample such as blood is smeared on a slide or substrate. A microscope locates the individual cells on the slide and their images are scanned, for example by television techniques. The two dimensional cell information, along with color, color density and the possibly fluorescence of the cell at many locations thereon are measured and stored in a computer memory. Algorithms are used for manipulating the stored data in an attempt to identify the cell.

Both techniques have been quite successful but not perfect. The former technique is fast but only measures the gross parameters. The latter technique is quite slow but provides rather thorough cell identification, although improvement is still possible. The information gleaned using the flow through technique may not be obtained when utilizing the pattern recognition technique and that information may be necessary for a complete positive cell identification.

An apparatus for automatic examination and separation of cells is described in the above-identified parent application. In one of the embodiments of that application a Coulter particle detector such as is described in U.S. Pat. No. 2,656,508 is combined with a particle separator such as is described in U.S. Pat. No. 3,380,584 to M. Fulwyler. In the apparatus of the parent application, particles in suspension move through the sensing zone of the particle detector, then through the Fulwyler type particle separator where the suspension is broken into discrete droplets containing the particles, then passed from the structure to a substrate. The information derived from the sensing of each particle is stored in a memory along with the time intervals between the sensed particles. The substrate is moved at a constant speed in a particular pattern so that the droplets and particles reach the substrate having a particular spatial pattern which is related to the time interval between sensed particles. This information is retained so that the particle characteristics and location on the substrate can be correlated. While the structure described is effective, the speed of the substrate must be accurately maintained in order to maintain a correct correlation between the time intervals of sensed particles and the spatial pattern formed on the substrate. Furthermore, the retention of the time information between particle sensings and the correlation with the spatial pattern on the substrate requires additional space in the computer memory and it is desirable to reduce the size of the computer memory and possibly eliminate the computer in order to reduce costs. In the embodiment described, all the particles are retained on the substrate, even those which may be of no interest, thus requiring large substrates whose surface areas are largely covered with particles of no interest.

A simple system which recognizes and detects the particle characteristics and then places the particles on a substrate in a specific pattern and correlates this pattern with the characteristics, without the need for determining the time relationships between particle occurrences, is desirable. A further economy of the desired system is that only particles sensed by the sensing zone would be preserved for further examination, thus reducing wasted substrate. Such a system allows rapid initial screening of particles such as cells, with retention of the cells of interest for later detailed analysis.

SUMMARY OF THE INVENTION

In practicing this invention, an apparatus is provided for identifying individual particles in a liquid suspension. The apparatus includes a particle scanning device which contains a quantity of suspension carrying particles. These particles are passed in a stream through a sensing zone in the particle scanning device which produces at least one characteristic signal representing at least one physical characteristic of each particle passed. The stream of particles in suspension is then passed out of the particle scanning device and the stream is broken into droplets with not more than one particle in any droplet. A substrate is positioned downstream of the particle scanning device. A sequencer is coupled to the scanning device and to the substrate and operates in response to at least one particular characteristic signal for each sensed particle to develop a sequence signal and to direct the stream and specific particle therein which produced the chracteristic signal. The droplet travels to a particular location on the substrate corresponding to the particular sequence signal. A memory, also coupled to the scanning device and the sequencer operates in response to receipt of at least one particular characteristic signal to store the characteristic signals for the particle and the sequence signal so that the particle location on the substrate and the particle characteristics are correlated.

The entire sequence of operation is inhibited during initialization of the apparatus operation and during and after each particle sensing and deflection in order to stabilize the apparatus operation and thus to ensure that only the sensed particle and no other is directed to the substrate location, and that the characteristics for the particle at that location and the sequence information for that location are properly correlated and stored.

BRIEF DESCRIPTION OF THE DRAWINGS

FIG. 2 is a block diagram representation of an embodiment of the apparatus of this invention.

DESCRIPTION OF THE PREFERRED EMBODIMENT

Figure 1:
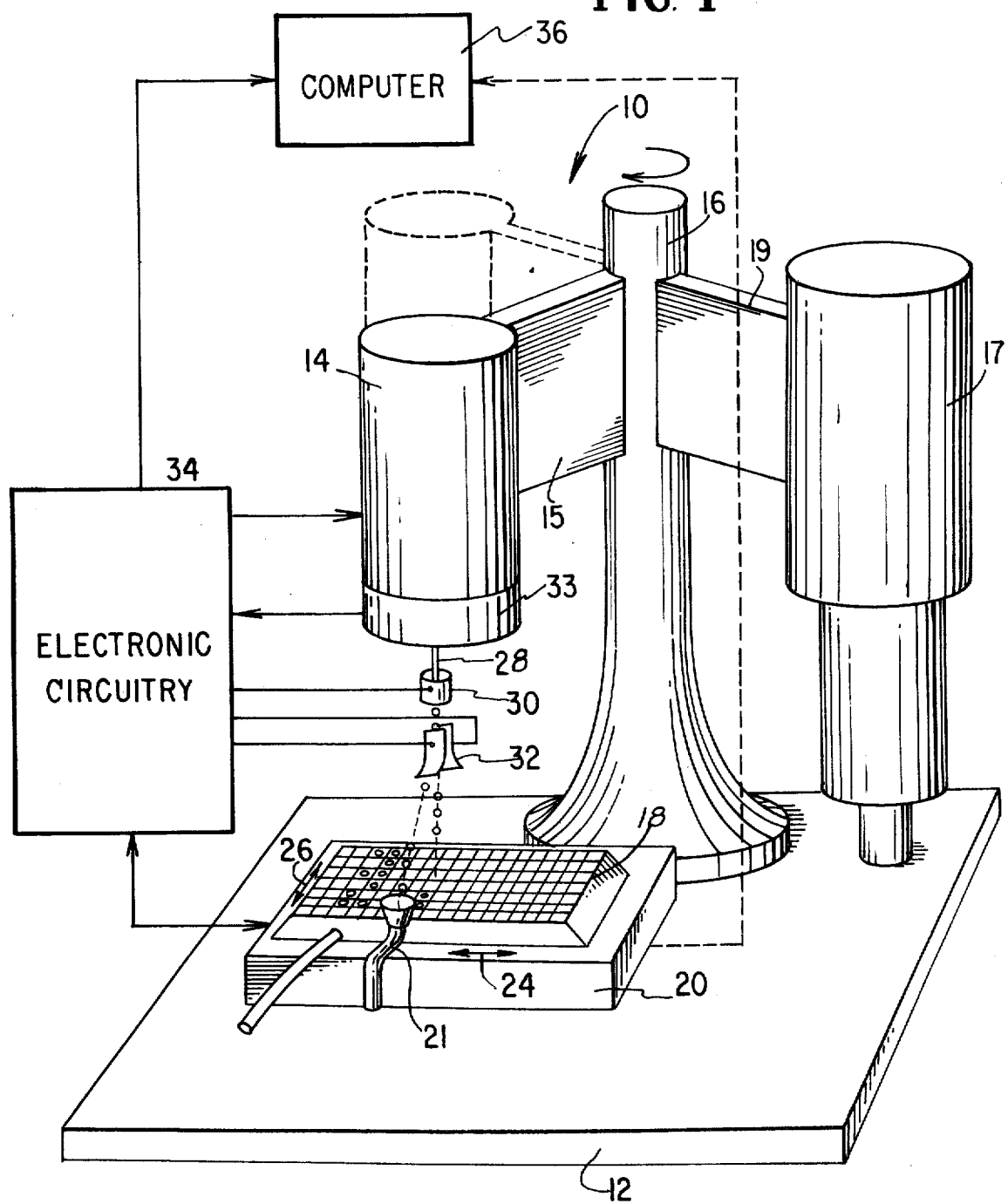
FIG. 1 is a combined diagrammatic and block diagram representation of the apparatus of this invention.

The basic components of the apparatus are first, a structure which is arranged to make measurements of a gross nature on particles carried in suspension as these particles are passed in succession through a sensing zone while deriving in addition a count sequence of particles of interest and storing them at memory locations specified by the count in the sequence; second, structure for projecting the particles after passing through the sensing zone in a stream against a substrate that moves relative to the stream in accordance with a predetermined plan based on that count sequence such that successive particles of interest are deposited at predetermined locations on the substrate, which locations are correlatable to the specified memory locations.

The practice of this invention contemplates that the measurements from the scanning of the particles by the sensing zone and the particle count or location information will be stored and made available for further measurements on the particle carried by the substrate either immediately or for future reference. Either by manual means or by automatic apparatus, the individual particle characteristics and particles on the substrate can be correlated with the results of further inspection and analysis of each particle. In this way, substantially more can be determined about any particular particle than could be derived from either the gross measurements produced by the sensing zone or microscopic examination (automatic or visual) alone.

Referring now to FIG. 1, the apparatus is generally designated by the reference number 10 and the mechanical and fluid components for the most part are shown mounted onto a base or platform 12. The particle scanning device 14 is shown mounted on an arm 15 of a standard 16. Standard 16 is rotatable in the directions indicated by the arcuate arrow and carries a microscope 17 on an arm 19 of standard 16. Particle scanning device 14 at least includes a sensing zone of the type described in Coulter Pat. No. 2,656,508 and a droplet generator of the construction detailed in Fulwyler Pat. No. 3,380,584. The droplet generator is arranged so that the droplets are ejected towards a substrate 18.

Substrate 18 is positioned downstream of scanning device 14. Substrate 18 has a surface that will retain any particles contained in droplets impinging thereon and will prevent their movement from their receiving location so that their positions remain substantially fixed upon impact. For example, the substrate may have a special surface of frosted or fritted glass or it may be made from absorbent material such as filter paper or porous rigid resins in order to enable the liquid of the droplets to be drawn away by suction and/or capillary action. Substrate 18 is mounted on a precision scanning stage 20.

The precision scanning stage 20 operates in response to indexing signals to move a predetermined amount in the X and Y directions indicated by arrows 24 and 26. The specific amount and directions moved in response to each indexing signal are preprogrammed by means built into the scanning stage. For example, the scanning stage may start from a first Y position and step twenty discrete steps in the Y direction indicated by arrow 26, then on the twenty first indexing signal it will move one step in the X direction indicated by arrows 24. The scanning stage may then return to the first Y position displaced one step in the X direction and repeat the steps through the Y positions. The stepping then defines a number of rectangularly spaced locations on the face of substrate 18, the boundaries of which are identified by the solid lines. Any particle may thus be located later by its X and Y coordinates. At the end of a predetermined number of indexing signals, representing a predetermined number of steps, for example, 1000, of scanning stage 20, it is programmed to stop, or return to an initial or starting position. If the stage is programmed to stop in the last position a separate reset signal must be provided in order to return the stage to the starting position. Each indexing signal supplied to scanning stage 20 can be a pulse which causes it to step or index one position to the following location in the sequence, or it can be a specific address identifier, preferably in digital form, which causes the table to sequence to a specific or predetermined location.

Referring again to particle scanning device 14, the droplet generator therein includes a jet forming orifice (not shown) located at the bottom of device 14. A stream 28 is ejected from the jet forming orifice in a manner which causes droplets to be formed at a predetermined distance below the orifice. The stream 28 and droplets pass through a droplet charging ring 30 and deflection plates 32.

Particles to be studied are suspended in an electrically conductive solution and introduced into the particle scanning device 14. In scanning device 14, the particles in suspension move one at a time through the sensing zone noted, causing the effective electrical impedance of the aperture to change in accordance with the volume of the particle. This changed impedance is sensed and employed to generate a signal whose amplitude is proportional to the size or volume of the particle passing through the aperture. The number of signals, their order of arrival and individual amplitudes can be stored for more detailed particle analysis.

Other information relating to particles can be obtained by transducing means responding to the passage of particles through electrical or optical sensing zones in liquid suspension. The so-called physical characteristics of the particles can be measured and recorded as electrical analog quantities and these physical characteristics may include response to aperture currents of multiple frequencies, response to different wavelengths of light, fluorescence, electrical opacity and so on. Fulwyler U.S. Pat. No. 3,710,933 describes several different characteristics that may be sensed.

Electronic circuitry for operating particle scanning device 14 and for receiving particle information therefrom; for operating charging ring 30, deflection plates 32 and scanning stage 20 is shown connected to the aforementioned items and identified by the reference number 34. The electronic circuitry 34 may be connected to a computer 36 or some other information storage device for storing the particle information and certain other information to be described hereafter.

In operation, the particle information, in the form of signals developed in particle scanning device 14, is coupled to electronic circuitry 34. The particle producing the received electronic signals exits in stream 28 by way of the jet forming orifice and is included in a droplet at charging ring 30 as explained in greater detail in the referenced Fulwyler patent. Each droplet contains no more than one particle and the time after receipt of the particle identifying information by electronic circuitry 34 at which the droplet containing the particle is formed can be identified. The droplet containing a particle will be directed to and impinge on substrate 18 at a particular location at this later time, only if the information received by the electronic circuitry 34 meets particular requirements, such as exceeding a particular threshold, and if the apparatus has stabilized by passage of a sufficient period of time after initialization or after recognition and direction of the last particle containing droplet. If any of the above conditions are not met, electronic circuit 34 applies a charging voltage to charging plate 30, and causes the droplets to be charged to a particular voltage. The charged droplets then pass through deflection plates 32 where they are deflected at a particular angle to a waste receptacle where they may be discarded or saved for later, further useage.

The signals received by electronic circuit 34 for that particle also cause a particular count signal to be developed. The count signal is coupled to the scanning stage 20 causing the stage to index to the next position in the indexing sequence so that the next droplet directed to substrate 18 impinges at the next location in the sequence. The count signal developed in electronic circuit 34 and the results of the measurements made on each particle, i.e., the particle signals developed by scanning device 14, are both coupled by electronic circuitry 34 to computer 36 so that the particle characteristics and the particle location on substrate 18 may be correlated.

At the end of a full operating sequence, when all of the locations on substrate 18 are filled or when the sample is entirely exhausted and the particles have been properly prepared, as for instance by staining and fixing microscope 17 can be rotated into position over substrate 18 for automatic particle inspection. The sequencer can then be activated to sequence scanning stage 20 to each location so that a pattern recognition scan can be performed as taught in the parent application, with the information so obtained and the information in the memory being collected as taught in the parent for accurate particle identification.

Referring now to FIG. 2, a more detailed block diagram of the apparatus is shown including a more detailed showing of the elements comprising electronic circuitry 34. Specifically, FIG. 2 shows a simple single parameter single-threshold embodiment. Particles to be studied such as blood cells are diluted in a fluid suspension and the fluid suspension is placed in a sample reservoir 40 which is part of the particle scanning device 14. It is assumed that air pressure and other necessary peripheral needs as described by Fulwyler and others are met. When device 14 is actuated the particles in suspension flow from reservoir 40 to and through one or more particle sensing zones and a jet forming orifice shown all represented in FIG. 2 by number 42. For purposes of this explanation, we shall assume for simplicity that it is desired to measure and record the volumes of all particles greater than a predetermined minimum and preserve these particles for further examination. If a Coulter type of particle detector is employed in the apparatus 42 as previously noted, particle pulses having amplitudes proportional to the particle volume will be developed in response to passage of each particle through the sensing zone. The particles in suspension exit device 14 through a jet forming orifice in the form of a stream 28 which breaks into droplets. This breakup occurs at charging plate 30. Because of the sample dilution chosen, a great many droplets are produced which contain no particles between droplets containing a particle. Also, the dilution ratio and droplet size are chosen such that a droplet will contain not more than one particle. Only certain ones of the particle containing droplets will be of interest.

The particle pulses developed by the passage of the particles through the sensing zone are amplified by amplifier 43 and coupled by way of conductor 44 to threshold circuit 46 and analog gate 48. Threshold circuit 46 is of the well known type which will develop a threshold pulse as soon as the signal received at its input exceeds a predetermined amplitude and will maintain this threshsold pulse until the input signal drops below the predetermined amplitude. We will assume for this example that the particle pulse developed exceeds the threshold level of threshold circuit 46 so that a threshold signal is developed consisting of a binary high state signal or a logical one at path 47. This description assumes a positive logic, i.e., a logical "one" is represented by a positive voltage or high state signal. Other logic is of course useable if compatible. This threshold signal is coupled to one input 52 of an AND gate 54.

The electronics circuitry 34 shown in FIG. 2 is initiated by presenting a start signal in the form of a high state binary signal at start input 62. This signal may be initiated in a number of ways such as, for example, by the use of a start switch and power source, it being understood that all portions of the apparatus including the droplet formation device and sensing zone are operating properly and that droplets are being directed to the waste receptacle. The high state signal is coupled from start input 62 to the reset input 64 of a counter 58 and to one input 66 of an OR gate 68.

The high state signal coupled to counter 58 will cause counter 58 to reset to zero count. Counter 58 counts from zero count to a predetermined number such as 1,000 and develops a different count signal for each count. This count signal is utilized to correlate the particle characteristics and the substrate location. Each count includes a number of signals, preferably digital, which are coupled to a memory 60 for addressing a particular memory location. When counter 58 counts to the prescribed number, it develops a high state signal at conductor 70 which is coupled via inverter input 72 to AND gate 54 presenting a low state signal to AND gate 54. Until this count is reached, a low state signal appears at conductor 70 so that the input at AND gate 54 before the desired total count is reached is a high state signal.

The start signal coupled from start input 62 to input 66 of OR gate 68 causes OR gate 68 to develop a high state signal which is coupled to the set input 74 of a bistable multivibrator 76, more commonly known as a flip-flop. Flip-flop 76 changes states in response to the signal at input 74 and develops a high state signal which is coupled to input 78 of AND gate 54.

The high state signal appearing at input 78 of AND gate 54 and the low state signal appearing at the inverter input 72 of AND gate 54 appear almost instantaneously after receipt of the high state signal and remain at these inputs so that upon receipt of the noted threshold signal at input 52 AND gate 54 changes states and develops a high state AND gate signal at its output which is coupled to delay circuit 80, trailing edge detector (T.E.D.) 81, the count input of counter 58 and control input 50 of analog gate 48.

The AND gate signal coupled to the control input 50 of analog gate 48 causes the analog gate to open and pass the part of the particle pulse which exceeds the threshold level fixed by threshold circuit 46 to the analog-to-digital converter, (A/D converter) and memory 60, thus allowing receipt of these pulses only after the apparatus is initialized and synchronized with the pulses and droplet formation. Any additional particle related characteristics developed by the other forms of sensing zones which may be employed at 42 in device 14 also are coupled by way of conductor 44, or other conductors not shown, through analog gates such as gate 48 (not shown) to A/D converter and memory 60 when opened by receipt of a gate signal at their gate inputs. The A/D converter and memory 60 converts the analog signals received from analog gate 48 and any other such gates to their digitally equivalent signals and stores these signals at the address designated by the count signal developed by counter 58.

The AND gate signal coupled to counter 58 is counted causing counter 58 to develop a count signal as previously discussed. This counting signal is passed to A/D converter and memory 60 for addressing the memory location where the particle characteristics are stored.

Trailing edge detector 81 operates in response to the trailing edge of the AND gate signal to develop a delayed trigger pulse which is coupled to a monostable multivibrator 82, more commonly known as a one shot. One shot 82 develops a high state signal of fixed amplitude and duration in response to the delayed trigger pulse which is coupled to T.E.D. 84. T.E.D. 84 operates in response to the termination of the high state signal from one shot 82 to develop a further delayed trigger pulse which is coupled to one shots 86 and 88 in order to provide a desired total delay period.

One shot 86 develops a shorting pulse that is coupled to a shorting device 87 which consists of a field effect transistor (F.E.T.) 89. The shorting pulses causes F.E.T. 89 to conduct and provide a low impedance path to ground potential. This low impedance path shorts out or reduces to a low value, the voltage normally coupled from voltage source 90 through resistor 91 to charging plate 30. The delay provided by the circuitry, T.E.D.'s 81 and 84 and one shot 82 causes the charge to be removed from the charging plate 30 at the time that the particle which produced the threshold pulse passes through charging plate 30 and a droplet is formed surrounding the particle so that the droplet containing the noted particle is not charged, and will then drop to substrate 18 at the particular location on substrate 18 corresponding to the count number noted previously. All other droplets will be charged by charging plate 30 and, when they pass through deflection plates 32 will be deflected to waste receptacle 21.

The AND gate signal developed at AND gate 54 is also coupled to delay circuit 80. Delay circuit 80 after a period of time sufficient to allow operation of T.E.D. 81 develops a high state signal at its output which is coupled to input 90, the reset input of flip-flop 76, causing flip-flop 76 to reset and terminate the high state signal coupled to input 78 of AND gate 54. Termination of the high state signal coupled to input 78 of AND gate 54 acts to inhibit AND gate 54 thus preventing operation of this circuitry and making it impossible for any subsequent particles to be directed to the substrate until such time as flip-flop 76 is again set. This occurs when the apparatus completes an operation cycle and stabilizes.

As noted previously, the pulse developed by trailing edge detector 84 also is coupled to a one shot 88. One shot 88 changes states in response to receipt of the pulse and develops a high or one state signal at its output for a predetermined time period. This predetermined time period is greater than the time period required for a droplet to move from the charging plate 30 to the substrate 18. The one shot 86 develops a charging pulse at its output of short duration, just sufficient to ensure that only the desired droplets passed uncharged. The high state signal developed by one shot 88 is coupled to a T.E.D. 92 which operates in response to the termination of the high state signal to develop a trailing edge pulse that is used to trigger a one shot 94. One shot 94 changes states in response to the received pulse and develops a high state indexing signal which is coupled to the previously mentioned programmed indexing mechanism 96, preferably a pair of programmed stepping motors, in scanning stage 20 causing the stage to index to the next position in the indexing sequence. Substrate 18 now is positioned for receipt of the next detected particle containing droplet.

A T.E.D. 97 also receives the high state signal developed by one shot 94, and develops a delayed trigger pulse in response to the trailing edge of the high state signal. The trigger pulse is coupled to a one shot 98 which develops a high state signal of fixed amplitude and duration. The high state signal developed by one shot 98 is coupled to a T.E.D. 100 which operates in response to the termination of this high state signal to develop a pulse that is coupled to another one shot 102. One shot 102 operates in response to the pulse received from T.E.D. 100 to develop a high state signal for a short period of time. This high state signal is coupled to the second input 104 of OR gate 68 causing OR gate 68 to develop a high state signal at its output that is coupled to the set input 74 of flip-flop 76.

The events described with respect to the operation of T.E.D.'s 97 and 100, one shots 98 and 102 and OR gate 68 take up a sufficient period of time to allow stabilization of indexing mechanism 96 and substrate 18 in their new location and to allow all vibrations to stop, and the stabilization of the remaining circuits in electronic circuitry 34, such as, for example, the termination of all operating transients. Flip-flop 76 responds to the high state signal received at set input 74 to change states and again develop a high state signal which is coupled to input 78 of AND gate 54. With the high state signal present at input 78, and so long as the full count has not been reached by counter 58, AND gate 54 operates in response to receipt of the next threshold signal received at input 52 to count the signal, store the count and particle characteristics in memory 60, direct the droplet entrapping the particle to the appropriate location on substrate 18, and then index scanning stage 20 and substrate 18 to its next location.

When an appropriate number of particles have been counted by counter 58 it develops a high state signal at its output which is coupled to an indicator 71. Indicator 71 provides an output for notifying personnel that the sample is to be changed and that it is necessary to initiate staining and/or microscopic review.

The high state signal from counter 58 is also coupled to input 72 of AND gate 54. The high state signal inhibits AND gate 54 preventing it from developing a high state signal at its output in response to receipt of any further threshold signals at input 52 and thus terminating operation of the electronic circuitry 34. At this time all of the programmed locations on substrate 18 have been filled with particles which have been selected and the particle characteristics and count number in the counting sequence have been stored in the memory. The information in the memory can be obtained by use of readout devices, commonly employed with such memories such as for example cathode ray tubes or printers. With the particle characteristics and count of the sequence known and with the substrate location corresponding to that count also known the particle characteristics and particle location can be correlated either manually or by appropriate indexing machines so that the individual particles may be further studied. Microscope 17 may be moved into position over substrate 18 and scanning stage 20 so that particles may be visually observed as the stage is indexed to each new location and the particle characteristics are displayed by the selected readout device.

Although a single embodiment has been shown and described with respect to FIGS. 1 and 2, it is to be understood that other modifications and variations are considered to be within the scope of this invention. For example, FIG. 2 shows the use of a single threshold circuit 46 in response to particle pulses that exceed a predetermined threshold. A window threshold circuit could be employed in place of threshold circuit 46 which would operate to develop a threshold signal only in response to pulses having an amplitude greater than a first predetermined amplitude and less than a second predetermined amplitude. Threshold circuit 46 can also operate in response to characteristic signals other than particle pulse signals produced by passage through a Coulter type aperture, for example, signals from an optical density or fluorescence detector, or a characteristic signal which is the combination of two or more of these signals. Substrate 18 need not be a rectangular plate but can be an elongate tape such as was described in the Parent application. When an elongate tape is used, it can index in one direction only as, for example, the direction indicated by arrow 26 in FIG. 1, thus moving the tape in a continuous path from a starting point of the tape to the end point. It is also possible to deflect droplets containing particles side by side to separate locations on the tape if the tape is of sufficient width, then index forward in the same manner as with substrate 18 and deposit droplet containing particles at the next locations in the sequence. It is possible to deflect the droplets differently for certain counts in the sequence so that the table is maintained stationary and not moved in the direction indicated by arrow 26.

In an alternate embodiment scanning stage 20 can be connected directly to computer 36 as shown by the dashed line in FIG. 1. The XY location for the scanning stage is fed to the computer 36 and provides the address for the particle information for the particle at that location. In this embodiment counter 58 in FIG. 2 acts only to count the total desired number and need not be connected to memory 60.

From the above noted embodiment and the modifications and variations noted, it should be clear that additional modifications and variations particularly of the specific blocks employed in electronic circuitry 34 are also considered to be within the scope of this invention.

What is claimed and desired to secure by Letters Patent in the United States is:

1. An apparatus for identifying particles in a liquid suspension comprising:
   a particle scanning device including, means for containing a quantity of suspension carrying particles, a sensing zone for producing at least one characteristic signal representing at least one physical characteristic of each particle passing therethrough, means for moving the suspension in a stream through the sensing zone and out of the particle scanning device such that particles separately pass therethrough and out,
   a substrate;
   sequencer means coupled to said scanning device and said substrate and operative in response to at least one characteristic signal for each particle to develop a particular sequence signal and to direct the stream and particle therein producing said characteristic signal to a particular location on said substrate corresponding to said particular sequence signal and;
   memory means coupled to said sensing means and said sequencer means and operative in response to said at least one characteristic signal to store said characteristic signal and one of said sequence signals and a memory location identifier corresponding to said substrate location, whereby each particle location and characteristic can be correlated.

2. The apparatus of claim 1 wherein said sequencer means include, indexing means for moving said substrate in a predetermined sequence determining a number of particular locations, said indexing means operative in response to each sequence signal to move to one of said particular locations.

3. The apparatus of claim 1 wherein said sequencer means include:
   threshold means coupled to said sensing means and operative in response to said at least one characteristic signal exceeding a threshold to develop a threshold signal;
   counter means coupled to said threshold means and operative to count each threshold signal and develop count signals for said count;
   direction means coupled to said threshold means and operative in response to said threshold signal to direct the stream and particle therein producing said threshold signal to said substrate; and
   indexing means coupled to said substrate and operative in response to the count signal for each count to move a step in a predetermined sequence whereby the substrate is moved in said sequence and said particle is deflected to a particular location on said substrate.

4. The apparatus of claim 3 wherein said counter means is a digital counter operative to count each threshold signal and develop a digital count signal for representing each accumulated count.

5. The apparatus of claim 3 wherein said memory means include converter means coupled to said sensing means for converting said characteristic signal to a digital number, a memory, gate means operative in response to said threshold signal to enter said digital number into said memory and to enter said count signal into said memory.

6. The apparatus of claim 3 wherein said sequencer means further include start means coupled to said counter means and said indexing means and operative upon actuation to develop a start signal, said counter means operative in response to said start signal to reset to an initial count, said indexing means operative to return to an initial location.

7. The apparatus of claim 6 wherein said start means is further coupled to said direction means, said direction means being operative upon receipt of said start signal to allow direction of said stream to said substrate in response to said threshold signal.

8. The apparatus of claim 3 wherein said direction means include charging means positioned adjacent said means for moving the suspension for charging said stream, said charging means operative in response to said threshold signal to remove the charge from the stream passing from said moving means and from the particle therein which produced said threshold signal, and deflection plates having a particular charge thereon positioned adjacent said stream after said charging means in the direction of stream flow for deflecting said charged stream, said uncharged droplet and particle therein passing without deflection to said substrate.

9. The apparatus of claim 8 wherein said means for moving the suspension include, droplet formation means for forming said suspension into a stream of droplets substantially each particle being contained in a single droplet, said stream of droplets passing through said charging means and deflection plates whereby said droplets containing no particles of interest are charged and deflected and particles of interest are uncharged and pass to said substrate.

10. The apparatus of claim 9 wherein said direction means include gate means coupled to said threshold means and counter means and operative in response to said threshold signal and a particular count signal to develop a gate signal and delay means coupled to said gate means and to said charging means and operative a predetermined time after said gate signal to develop a first delay signal, said charging means operative in response to said first delay signal to inhibit charging the droplet and particle therein which produced such signal whereby said droplet and particle are passed to said substrate.

11. The apparatus of claim 10 wherein said sequencer means further include start means coupled to said counter means and said indexing means and operative upon actuation to develop a start signal, said counter means operative in response to said start signal to reset to an initial count.

12. The apparatus of claim 11 wherein said start means further is coupled to said gate means, said gate means being operative in response to said threshold signal, said particular count and said start signal to develop said gate signal.

13. The apparatus of claim 12 wherein said direction means include, second delay means coupled to said indexing means and operative at a predetermined time after said gate signal to develop a second delay signal, said indexing means operative in response to said second delay signal to index the next step in said sequence.

14. The apparatus of claim 13 wherein said direction means include third and fourth delay means coupled to said start means, said third delay means operative a third predetermined time after said gate signal to develop a third delay signal, said start means operative in response to said third delay signal to terminate said start signal, said fourth delay means being operative a fourth predetermined time, greater than said third predetermined time, after said gate signal to develop a fourth delay signal, said start means operative in response to said fourth delay signal to develop said start signal.

15. The apparatus of claim 14 wherein said start means include actuation means operative upon actuation to develop an actuation signal, second gate means coupled to said actuation means and said fourth delay means and operative in response to said one of said actuation signal and said fourth delay signal to develop a second gate signal, switch means coupled to said second gate means, said third delay means and said gate means and operative in response to said second gate signal to develop said start signal and operative in response to said third delay signal to terminate said start signal.

16. The apparatus of claim 3 wherein said direction means include, gate means coupled to said threshold means and counter means and operative in response to said threshold signals and a particular count signal to develop a gate signal, delay means coupled to said gate means and operative in response to said gate signal to develop a first delay signal, and charging means coupled to said delay means and operative in response to said delay signal to inhibit charging said stream whereby said stream portion is not deflected and is passed to said substrate.

17. The apparatus of claim 16 wherein said direction means include, second delay means coupled to said indexing means and operative a predetermined time after said gate signal to develop a second delay signal, said indexing means operative in response to said second delay signal to index the next step in said said sequence.

18. The apparatus of claim 16 wherein said direction means include third and fourth delay means coupled to said start means, said third delay means operative a third predetermined time after said gate signal to develop a third delay signal, said start means operative in response to said third delay signal to terminate said start signal, said fourth delay means being operative a fourth predetermined time, greater than said third predetermined time after said gate signal to develop a fourth delay signal, said start means operative in response to said fourth delay signal to develop said start signal.

19. An apparatus for identifying particles in a liquid suspension comprising:
   means for measuring at least one particular characteristic of each of said particles as said particles are passed therethrough;
   droplet generating means for forming droplets of the liquid suspension such that the number of droplets containing more than one particle of interest to be identified is substantially zero;
   means for counting each particle measured and identifying the count number;
   means for depositing particles having said particular characteristic on a substrate and at particular locations thereon, each location being associated with a particular identified count;
   means for storing said characteristic and one of said count and an identifier corresponding to said count;
   means for moving the substrate in a particular sequence;
   means for synchronizing the substrate sequence and the count.

20. An apparatus for identifying particles in a liquid suspension comprising:
   sensing means for measuring at least one particular characteristic of each particle in said suspension and for developing characteristic signals therefrom;
   droplet formation means for forming droplets of said liquid suspension, substantially each particle being contained in a single separate droplet;
   a substrate;
   sequencer means coupled to said sensing means and said substrate and operative in response to at least one of said characteristic signals for each particle to develop a particular sequence signal and to direct the droplet and particle therein producing said characteristic signal to a particular location on said substrate corresponding to said particular sequence signal; and
   memory means coupled to said sensing means and said sequencer means and operative in response to said at least one particular characteristic signal to store said characteristic signal and one of said sequence signal and a memory location identifier corresponding to said substrate location whereby each particle location and characteristic is correlated.

21. The apparatus of claim 20 further including visual inspection means for visually observing said particles at said particular location, said sequencer means being operative to sequence to each particular location on said substrate for allowing said visual observation.

22. The apparatus of claim 21 wherein said visual observation means is a microscope.

23. The apparatus of claim 20 further including automatic inspection means for automatically inspecting said particles at said particular locations, said sequencer means being operative to sequence to each particular location on said substrate for allowing said automatic inspection.

24. The apparatus of claim 23 wherein said automatic inspection means performs a pattern recognition scan at each of said particular locations.

25. The apparatus of claim 24 wherein results of said pattern recognition scan are correlated with said at least one particular characteristic.

26. The apparatus of claim 19 further including visual inspection means for visually observing said particles at said particular location, said substrate moving means being operative to sequence to each particular location on said substrate for allowing said visual observation.

27. The apparatus of claim 26 wherein said visual observation means is a microscope.

28. The apparatus of claim 26 further including automatic inspection means for automatically inspecting said particles at said particular locations, said substrate moving means being operative to sequence to each particular location on said substrate for allowing said automatic inspection.

29. The apparatus of claim 28 wherein said automatic inspection means performs a pattern recognition scan at each of said particular locations.

30. The apparatus of claim 29 wherein results of said pattern recognition scan are correlated with said at least one particular characteristic.

* * * * *